US009778376B2

(12) United States Patent
Okada

(10) Patent No.: US 9,778,376 B2
(45) Date of Patent: Oct. 3, 2017

(54) RADIOGRAPHIC IMAGING DEVICE, RADIOGRAPHIC IMAGING SYSTEM, COMPUTER READABLE MEDIUM STORING PROGRAM FOR CONTROLLING RADIOGRAPHIC IMAGING DEVICE, AND METHOD FOR CONTROLLING RADIOGRAPHIC IMAGING DEVICE

(71) Applicant: FUJIFILM CORPORATION, Minato-ku, Tokyo (JP)

(72) Inventor: Yoshihiro Okada, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 0 days.

(21) Appl. No.: 14/972,117

(22) Filed: Dec. 17, 2015

(65) Prior Publication Data
US 2016/0103229 A1    Apr. 14, 2016

Related U.S. Application Data

(63) Continuation of application No. 13/468,040, filed on May 10, 2012, now Pat. No. 9,250,333.

(30) Foreign Application Priority Data

May 10, 2011  (JP) ................................ 2011-105387
Apr. 18, 2012  (JP) ................................ 2012-095084

(51) Int. Cl.
*A61B 6/00*       (2006.01)
*G01T 1/17*       (2006.01)
(Continued)

(52) U.S. Cl.
CPC ............... *G01T 1/17* (2013.01); *G01N 23/04* (2013.01); *H04N 5/32* (2013.01); *A61B 6/4233* (2013.01); *A61B 6/542* (2013.01)

(58) Field of Classification Search
CPC ......... A61B 6/4233; A61B 6/542; G01T 1/17; G01T 1/24; H04N 5/32; G01N 23/04
See application file for complete search history.

(56) References Cited

U.S. PATENT DOCUMENTS 6,307,915 B1 * 10/2001  Frojdh ...................... G01T 1/17
                                                  348/E3.02
9,250,333 B2 *  2/2016  Okada ...................... G01T 1/17
(Continued)

FOREIGN PATENT DOCUMENTS

JP    2006-125872 A    5/2006
JP    2006-246961 A    9/2006
(Continued)

OTHER PUBLICATIONS

Translation of WO 2010/150569, published in 2010.*
(Continued)

*Primary Examiner* — Glen Kao
(74) *Attorney, Agent, or Firm* — SOLARIS Intellectual Property Group PLLC

(57) ABSTRACT

The present invention provides a radiographic imaging device, radiographic imaging system, a program for controlling the radiographic imaging device, and a method for controlling the radiographic imaging device that may accurately detect start of irradiation of radiation even noises are generated by interference or the like. When radiation is irradiated, electric signals outputted from radiation detection pixels in charge accumulation period are detected by signal detection circuit during detection period. Control section determines whether time variation of the electric signals feature pre-specified characteristics of noise. If not, the start of the irradiation of radiation has been properly detected, the charge accumulation period continues, and radiographic image is imaged. However, if the electric signals feature the pre-specified characteristics, it is determined that the start of
(Continued)

the irradiation of radiation has been misdetected, the charge accumulation period is stopped, and is switched to radiation detection period.

7 Claims, 14 Drawing Sheets

(51) Int. Cl.
*H04N 5/32* (2006.01)
*G01N 23/04* (2006.01)

(56) References Cited

U.S. PATENT DOCUMENTS

| | | |
|---|---|---|
| 2002/0050568 A1 | 5/2002 | Nonaka |
| 2008/0198969 A1 | 8/2008 | Taoka |
| 2012/0288061 A1 | 11/2012 | Okada |

FOREIGN PATENT DOCUMENTS

| | | |
|---|---|---|
| JP | 2008-132216 A | 6/2008 |
| JP | 2010-268171 A | 11/2010 |
| JP | 2011-62425 A | 3/2011 |
| WO | 2006-095714 A1 | 9/2006 |
| WO | 2010-150569 A1 | 12/2010 |

OTHER PUBLICATIONS

Kuphaldt et al., "Logic signal voltage levels", All about Circuits, vol. IV -Digital Chapter 3: Logic Gates, (Apr. 11, 2010). Retrieved from the Internet <http://web.archive.org/web/20100411190452/http://wwwallaboutcircuits.com/vol_4/chpt_3/10.html>.

Japanese Office Action dated Jul. 29, 2014 issued in the corresponding Japanese Patent Application No. 2012-095084.

Non-Final Office Action dated Apr. 25, 2014 issued in the U.S. Appl. No. 13/468,040.

Non-Final Office Action dated Oct. 7, 2014 issued in the U.S. Appl. No. 13/468,040.

Final Office Action dated May 8, 2015 issued in the U.S. Appl. No. 13/468,040.

English language translation of the following: Office action dated Feb. 9, 2016 from the JPO in a Japanese patent application corresponding to the instant patent application.

* cited by examiner

FIG.10
(1)
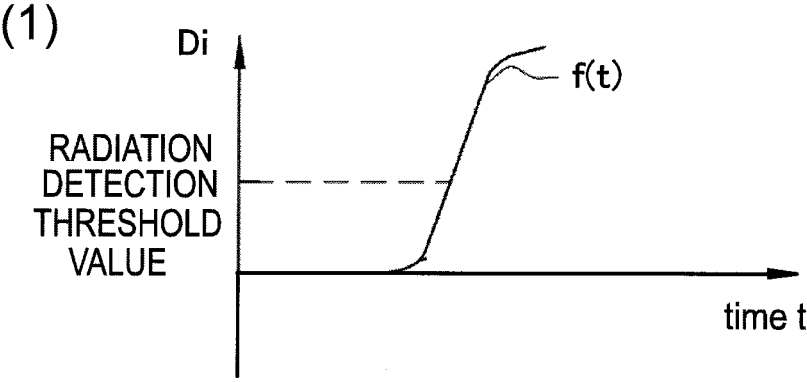
(2)
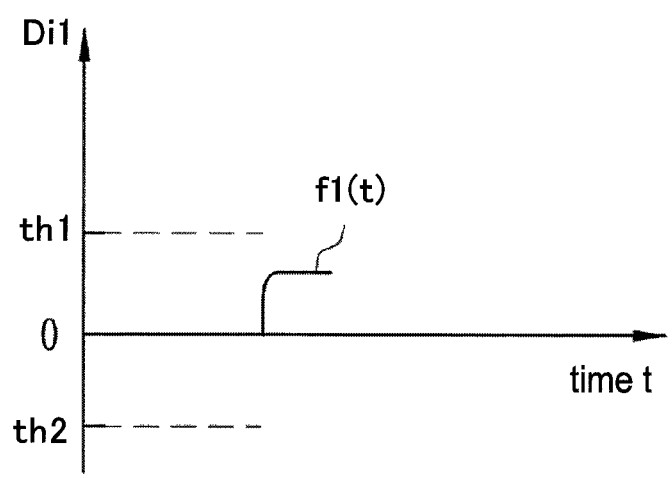
(3)
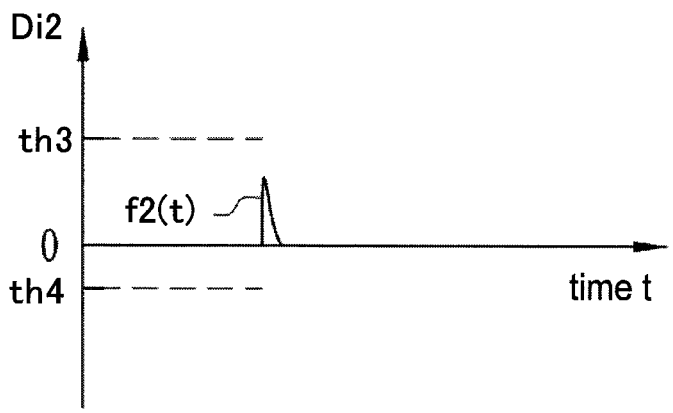

RADIOGRAPHIC IMAGING DEVICE, RADIOGRAPHIC IMAGING SYSTEM, COMPUTER READABLE MEDIUM STORING PROGRAM FOR CONTROLLING RADIOGRAPHIC IMAGING DEVICE, AND METHOD FOR CONTROLLING RADIOGRAPHIC IMAGING DEVICE

CROSS-REFERENCE TO RELATED APPLICATIONS

This application is a continuation of, and claims the benefit of, prior U.S. application Ser. No. 13/468,040, filed on May 10, 2012, which claims priority under 35 USC 119 from Japanese Patent Applications No. 2011-105387, filed on May 10, 2011, and No. 2012-095084, filed on Apr. 18, 2012. The entire disclosure of each application listed above is incorporated by reference herein.

BACKGROUND OF THE INVENTION

Field of the Invention

The present invention relates to a radiographic imaging device, a radiographic imaging system, a computer readable medium storing a program for controlling a radiographic imaging device, and a method for controlling a radiographic imaging device. The present invention particularly relates to a radiographic imaging device, radiographic imaging system, computer readable medium storing a program for controlling a radiographic imaging device, and a method for controlling a radiographic imaging device, for imaging radiographic images for medical purposes.

Heretofore, a radiographic imaging device that performs radiographic imaging for purposes of medical diagnostics has been known. This radiographic imaging device detects radiation that has been irradiated from a radiation irradiation device and transmitted through an imaging subject, and images a radiographic image. The radiographic imaging device images the radiographic image by collecting and reading out charges that are generated in accordance with the irradiated radiation.

This radiographic imaging device is known to be provided with sensor portions, formed of optoelectronic conversion elements or the like, switching elements, and a detection section. The sensor portion generates charges due to irradiation of radiation or illumination of light that has been converted from the radiation. The switching elements read out the charges generated in the sensor portion. The detection section detects that the start of the irradiation of the radiation (start of imaging of the radiographic image) in accordance with the charges read out from the switching elements.

In this radiographic imaging device that includes the detection section, the detection section may misdetect the start of the irradiation of the radiation, in a case in which charges are generated in the sensor portions by, for example, an impact or noises caused by interference from electromagnetic waves, or the like.

Accordingly, there are technologies that prevent this misdetection. For example, Japanese Patent Application Laid-Open (JP-A) No. 2010-268171 discloses a radiographic imaging device that detects the start of the irradiation of the radiation on the basis of a value of current flowing in a bias line. This radiographic imaging device may prevent a rise in the voltage value in the bias line, occurred by noises when an ON voltage or OFF voltage applied to a switching element is superposed on the current flowing in the bias line, from being misdetected as the start of an irradiation of radiation.

Further, JP-A No. 2006-246961 discloses an X-ray imaging device. This X-ray imaging device may avoid misdetections due to noises, and may properly detect imaging start timings, whether the X-ray radiation is periodic radiation based on a half-wave waveform rectified from an AC power source voltage, or steady radiation based on a voltage waveform that is a straight DC voltage provided by a high-frequency inverter system.

However, in the technologies described above, time may be needed to determine that the detection portion has misdetected the start of the irradiation of the radiation, and may not detect the actual start of the irradiation of the radiation for imaging a radiographic image, due to this time. Accordingly, even if noises are generated due to interference or the like, accurate detections of the start of irradiations of the radiation that do not take time, are desired.

SUMMARY OF THE INVENTION

The present invention provides a radiographic imaging device, radiographic imaging system, program for controlling radiographic imaging device and method for controlling a radiographic imaging device that may accurately detect the start of irradiations of radiation, even if noises are generated due to causes of interference or the like.

A first aspect of the present invention is a radiographic imaging device including: a plurality of pixels, each pixel including, a sensor portion that generates charges in accordance with irradiated radiation, and a switching element that, in accordance with the control signals, reads out the charges from the sensor portion and outputs electric signals according to the charges to a signal line; radiation detection elements, that are pixels among the plurality of pixels having the switching elements short-circuited, and that output electric signals according to charges generated due to irradiated radiation; a detection section that detects the start of an irradiation of the radiation on the basis of the electric signals outputted from the radiation detection elements in a detection period; a control signal output section that outputs the control signals that control the read out of the charges; and a determination section that, in a radiographic imaging period after the detection section has detected the start of the irradiation of the radiation, detects the electric signals outputted from the radiation detection elements and, on the basis of a time variation of the detected electric signals, determines whether or not the detection section has misdetected the start of the irradiation of radiation.

The detection section detects the start of the irradiation of radiation on the basis of the electric signals outputted from the radiation detection elements in the detection period. However, in a case in which noises (electric signals) are generated due to causes of interference or the like, the detection section may misdetect the start of the irradiation of the radiation.

According to the first aspect of the present invention, the determination section detects the electric signals outputted from the radiation detection elements in the radiographic imaging period, after the detection of the start of irradiation of the radiation. The determination section then determines whether or not the detection section has misdetected the start of the irradiation of the radiation, on the basis of the time variation of the detected electric signals.

Electric signals that are noises caused by interference have the characteristic that time variation are different from electric signals during usual radiographic imaging. In the first aspect of the present invention, the determination section determines whether the start of the irradiation of radiation has been misdetected on the basis of the time variation of the detected electric signals. Therefore, the first aspect of the present invention may detect the start of an irradiation of radiation accurately even if noises due to interference or the like are generated.

A second aspect of the present invention, in the above aspect, the determination section may determine whether the detection is a misdetection, on the basis of a time variation of at least one of a polarity of the charges according to the detected electric signals, and amplitudes of a waveform that expresses the time variation of amounts of the charges.

A third aspect of the present invention, in the above aspects, the determination section may determine whether the detection is a misdetection, on the basis of a value predetermined for each of predefined signal lines.

A fourth aspect of the present invention, in the above aspects, may further include: a control section that, in the imaging period, outputs control signals that prohibits the extraction of charges from the pixels and, after the imaging period has ended, controls the control signal output section to output the control signals so as to extract the charges; and a switching section that switches from the detection period to the imaging period in a case in which the detection section detects the start of the irradiation of radiation, and, after switching to the imaging period, switches from the imaging period to the detection period in a case in which the determination section determines that the detection is a misdetection.

A fifth aspect of the present invention, in the above forth aspect, in a case in which the determination section determines that the detection is a misdetection, and in a case in which the switching section has switched from the imaging period to the detection period, the control section may control the control signal output section to perform a reset operation that extracts the charges from the plurality of pixels by outputting the control signals to perform an extraction of charges.

A sixth aspect of the present invention, in the above aspects, may further include an output section that outputs the electric signals read out from the plurality of pixels in the imaging period, and in a case in which the determination section determines that the detection is a misdetection, may discard the electric signals extracted from the plurality of pixels without outputting the electric signals.

A seventh aspect of the present invention is a radiographic imaging system including: an irradiation device that irradiates radiation; and a radiographic imaging device according to the above aspects that images a radiographic image in accordance with the radiation irradiated from the irradiation device.

An eighth aspect of the present invention is a radiographic imaging system including: an irradiation device that irradiates radiation; a radiographic imaging device according to the fifth aspect that images a radiographic image in accordance with the radiation irradiated from the irradiation device; and a control device that performs control so as to prohibit the irradiation of radiation by the irradiation device during the reset operation of the radiographic imaging device.

A ninth aspect of the present invention is a method for controlling a radiographic imaging device including, a plurality of pixels, each pixel including, a sensor portion that generates charges in accordance with irradiated radiation, and a switching element that, in accordance with the control signals, reads out the charges from the sensor portion and outputs electric signals according to the charges to a signal line, radiation detection elements, that are pixels among the plurality of pixels having the switching elements short-circuited, and that output electric signals according to charges generated due to irradiated radiation, a detection section that detects the start of an irradiation of the radiation on the basis of the electric signals outputted from the radiation detection elements in a detection period, a control signal output section that outputs the control signals that control the read out of the charges, and a determination section that, in a radiographic imaging period after the detection section has detected the start of the irradiation of the radiation, detects the electric signals outputted from the radiation detection elements and, on the basis of a time variation of the detected electric signals, determines whether or not the detection section has misdetected the start of the irradiation of radiation, the method including: detecting the electric signals outputted from the radiation detection elements in a radiographic imaging period after the detection section has detected the start of the irradiation of radiation; and, determining whether or not the detection section has misdetected the start of the irradiation of radiation, on the basis of a time variation of the detected electric signals.

A tenth aspect of the present invention is a computer readable medium storing a program causing a computer to execute a process for controlling a radiographic imaging device including, a plurality of pixels, each pixel including, a sensor portion that generates charges in accordance with irradiated radiation, and a switching element that, in accordance with the control signals, reads out the charges from the sensor portion and outputs electric signals according to the charges to a signal line, radiation detection elements, that are pixels among the plurality of pixels having the switching elements short-circuited, and that output electric signals according to charges generated due to irradiated radiation, a detection section that detects the start of an irradiation of the radiation on the basis of the electric signals outputted from the radiation detection elements in a detection period, a control signal output section that outputs the control signals that control the read out of the charges, and a determination section that, in a radiographic imaging period after the detection section has detected the start of the irradiation of the radiation, detects the electric signals outputted from the radiation detection elements and, on the basis of a time variation of the detected electric signals, determines whether or not the detection section has misdetected the start of the irradiation of radiation, the process including: detecting the electric signals outputted from the radiation detection elements in a radiographic imaging period after the detection section has detected the start of the irradiation of radiation; and, determining whether or not the detection section has misdetected the start of the irradiation of radiation, on the basis of a time variation of the detected electric signals.

The noises disclosed in JP-A No. 2010-268171 are generated when an ON voltage or OFF voltage is applied to a switching element is superposed on the current flowing in the bias line, based on the reset operation. Accordingly, these noises have a specific cycle that can be anticipated. Therefore, these noises may be removed by providing band pass filters (BPFs) or low pass filters (LPFs), and by configuring to output the current in the bias lines via the BPFs or LPFs. However, the noises generated due to interference or the like, are generated unexpectedly and irregularly, and therefore, may not be removed by the BPFs or LPFs. Accordingly, the present invention focuses onto the noise generated due to interference or the like.

As described above, according to the above aspects, the present invention may accurately detect the start of the irradiation of the radiation, even if noise is generated due to causes of interference or the like.

BRIEF DESCRIPTION OF THE DRAWINGS

Exemplary embodiments of the present invention will be described in detail based on the following figures, wherein:

FIG. 10 is a graph showing time variations of the electric signals when radiation is irradiated to the radiographic detector according to the present exemplary embodiment;

DETAILED DESCRIPTION OF THE INVENTION

Hereinbelow, exemplary embodiments of the present invention will be described with reference to the drawings.

Figure 1:
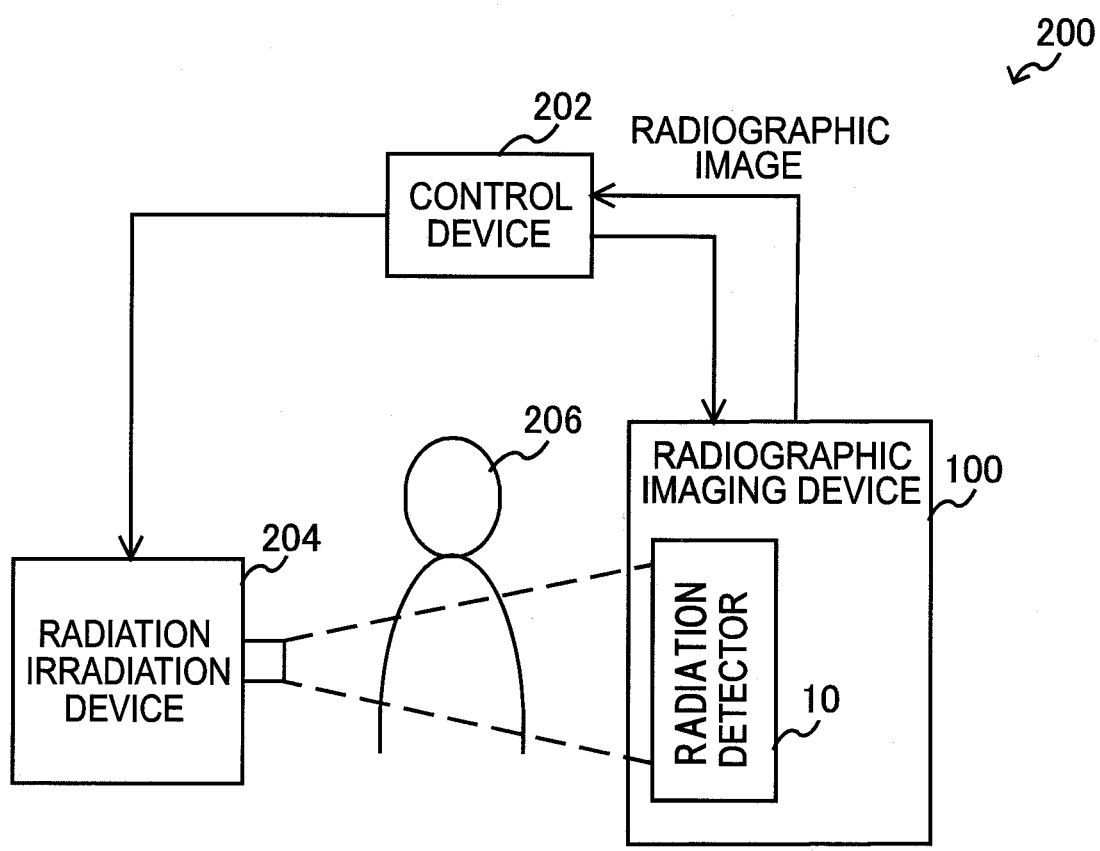
FIG. 1 is a schematic configurational diagram showing a radiographic imaging system according to a present exemplary embodiment.

Firstly, configuration of a radiographic imaging system that employs a radiographic imaging device of the present exemplary embodiment will be described. FIG. 1 is a schematic configurational diagram of an example of the radiographic imaging system of the present exemplary embodiment.

A radiographic imaging system 200 is configured including a radiation irradiation device 204, a radiographic imaging device 100 equipped with a radiation detector 10, and a control device 202. The radiation irradiation device 204 irradiates radiation (for example, X-rays or the like) at an imaging subject 206. The radiation detector 10 detects radiation that has been irradiated from the radiation irradiation device 204 and transmitted through the imaging subject 206. The control device 202 instructs imaging of a radiographic image and acquires a radiographic image from the radiographic imaging device 100. Radiation irradiated from the radiation irradiation device 204 at a timing in accordance with control by the control device 202 is transmitted through the imaging subject 206 positioned at an imaging position, and the transmitted radiation that carries image information is irradiated onto the radiographic imaging device 100.

Next, configuration of the radiographic imaging device 100 of the present exemplary embodiment is described. In the present exemplary embodiment, a case in which the present invention is applied to the radiation detector 10 of an indirect-conversion-type, in which radiation of X-rays or the like is temporarily converted to light, and the converted light is then converted to electric charges, will be described. In the present exemplary embodiment, the radiographic imaging device 100 is configured to include the indirect-conversion-type radiation detector 10. Note that a scintillator that converts the radiation to light is not shown in FIG. 2.

In the radiation detector 10, plural pixels 20 that each include a sensor portion 103 and a TFT switch 4, are arranged in a matrix pattern. The sensor portion 103 receives light and generates charges, and accumulates the generated charges. The TFT switch 4 is a switching element for reading out the charges accumulated in the sensor portion 103. In the present exemplary embodiment, the sensor portion 103 generates charges when irradiated with light converted by the scintillator.

Figure 2:
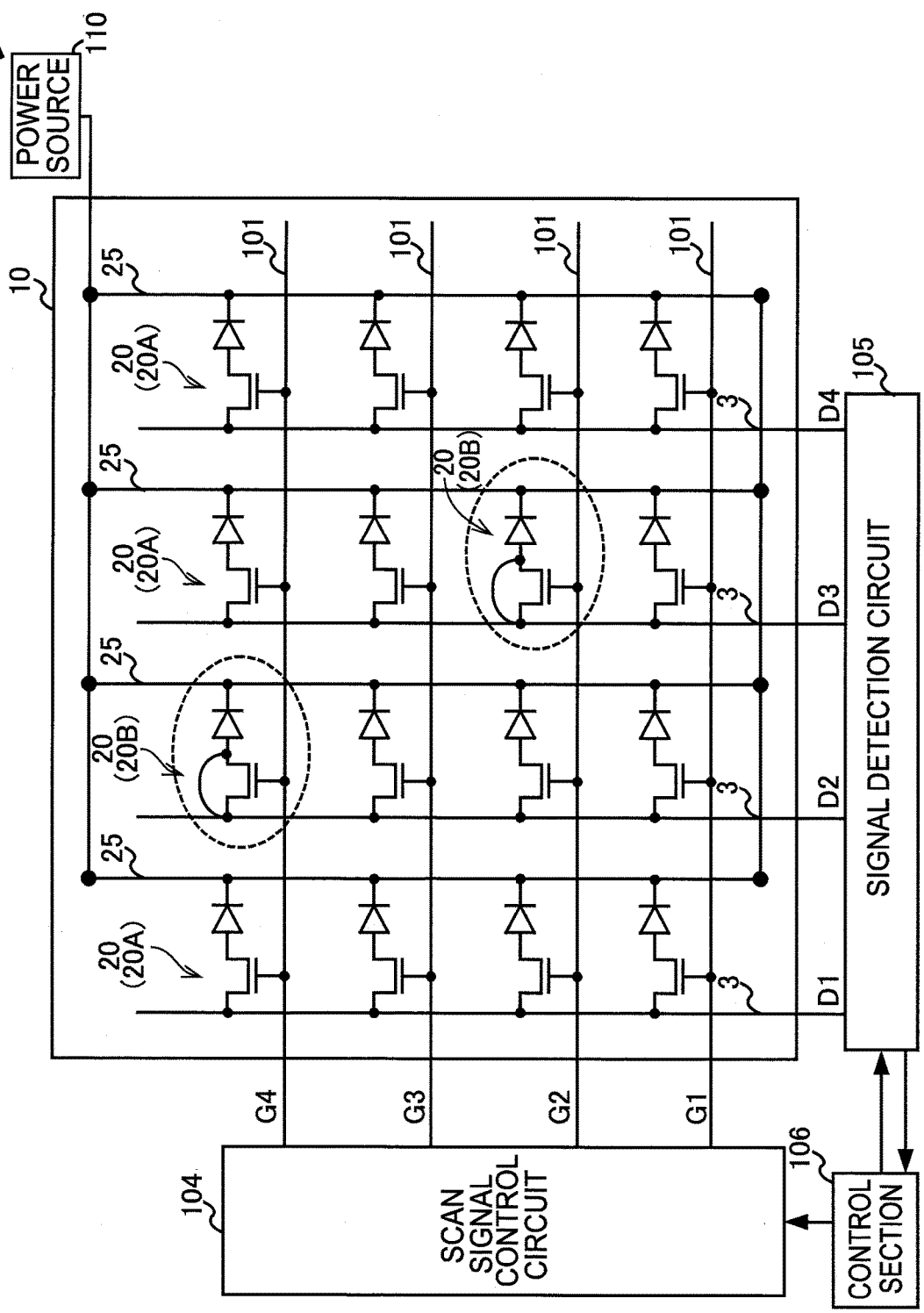
FIG. 2 is a configurational diagram showing the whole of a radiographic imaging device according to the present exemplary embodiment.

The pixels 20 are plurally arranged in the matrix in one direction (the direction of scan lines 101 in FIG. 2, which is the horizontal direction in FIG. 2), and a direction intersecting the scan line direction (the direction of signal lines 3 in FIG. 2, which is the vertical direction in FIG. 2). Note that the arrangement of the pixels 20 is simplified in FIG. 2, and for example, the pixels 20 may be arranged in 1024, in scan line direction, by 1024, in signal line direction.

In the present exemplary embodiment, among the plural pixels 20, pixels for radiographic imaging 20A (radiographic imaging pixels) and pixels for radiation detection 20B (radiation detection pixels) are specified in advance. In FIG. 2, the radiation detection pixels 20B are encircled by broken lines. The radiographic imaging pixels 20A are used for detecting radiation and for generating an image representing the radiation. The radiation detection pixels 20B are pixels that are used for detecting radiation, and that output charges even in a charge accumulation period.

Figure 3:
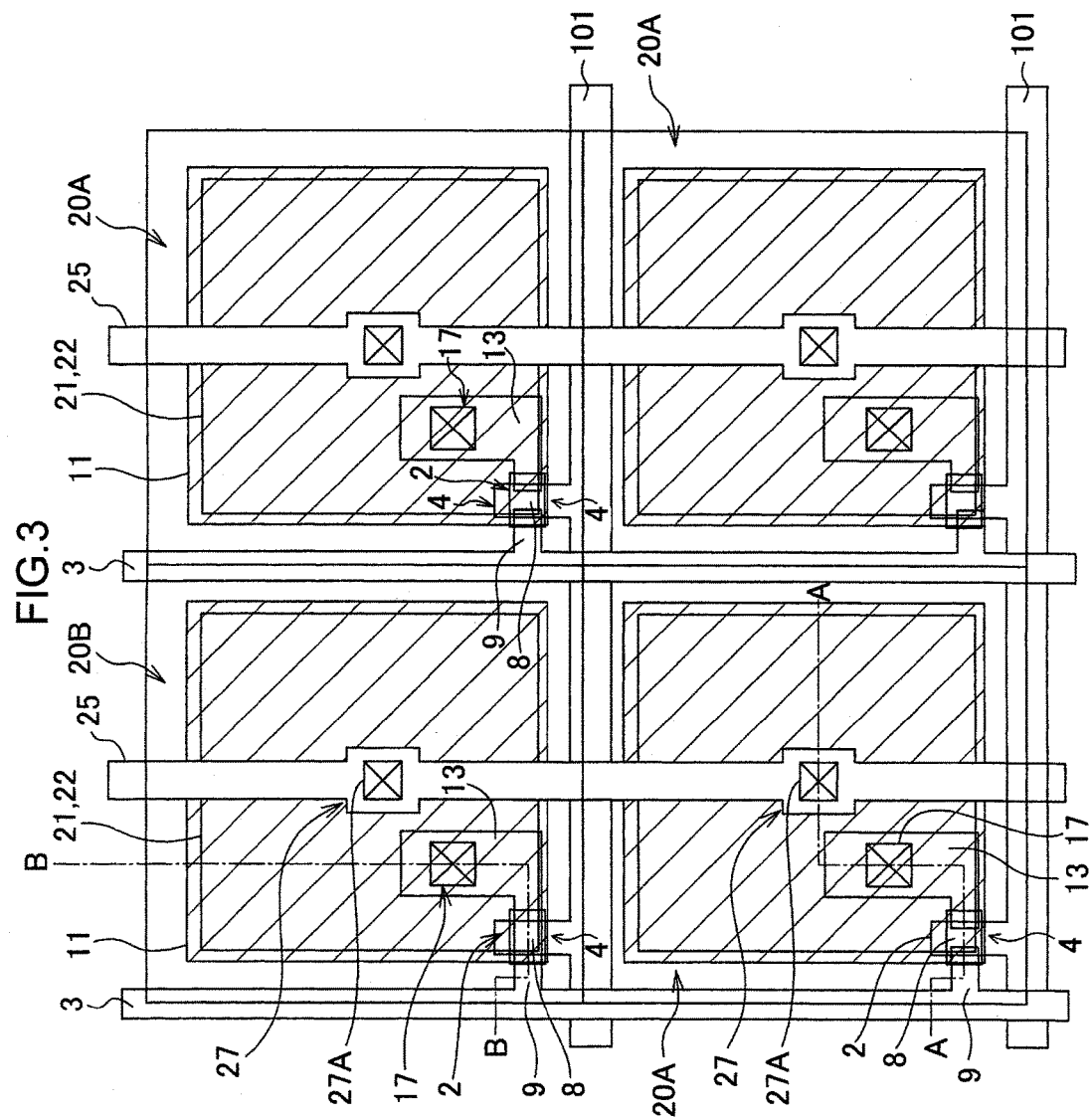
FIG. 3 is a plan view illustrating configurations of radiation detector according to the present exemplary embodiment.

In the radiation detector 10, a plural number of the scan lines 101 and a plural number of the signal lines 3 are provided to intersect with each other on a substrate 1 (see FIG. 3). The scan lines 101 switch the TFT switches 4 ON and OFF. The signal lines 3 read out charges accumulated in the sensor portions 103. In the present exemplary embodiment, one signal line 3 is provided for each pixel line in the one direction, and one scan line 101 is provided for each pixel line in the intersecting direction. For example, if the pixels 20 are arranged in 1024, in scan line direction, by 1024, in signal line direction, 1024 each of the signal lines 3 and the scan lines 101 are provided.

In the radiation detector 10, common electrode lines 25 are provided in parallel with the signal lines 3. One ends and other ends of the common electrode lines 25 are connected in parallel. The one ends are connected to a power source 110 that supplies a predetermined bias voltage. The sensor portions 103 are connected to the common electrode lines 25, and the bias voltage is applied to the sensor portions 103 via the common electrode lines 25.

Control signals for switching the TFT switches 4 flow through the scan lines 101. Accordingly, the TFT switches 4 are switched by these control signals flowing in the scan lines 101.

Electric signals corresponding to the charges accumulated in the pixels 20 flow into the signal lines 3 in accordance with switching states of the TFT switches 4 of the pixels 20. More specifically, when the TFT switch 4 of one of the pixels 20 connected to one of the signal lines 3 is switched ON, an electric signals corresponding to an accumulated charge amount flows into that signal line 3.

A signal detection circuit 105, which detects the electric signals flowing in the signal lines 3, is connected to the signal lines 3. A scan signal control circuit 104, which outputs control signals for switching the TFT switches 4 ON and OFF to the scan lines 101, is connected to the scan lines 101. FIG. 2 is simplified to show a single signal detection circuit 105 and a single scan signal control circuit 104. However, for example, the signal detection circuit 105 and the scan signal control circuit 104 may be plurally provided and predetermined numbers (for example, 256) of the signal lines 3 and the scan lines 101 may be connected to the respective signal detection circuits 105 and scan signal control circuits 104. For example, if 1024 each of the signal lines 3 and the scan lines 101 are provided, four of the scan signal control circuits 104 may be provided and sets of 256 of the scan lines 101 may be connected thereto, and four of the signal detection circuits 105 may be provided and sets of 256 of the signal lines 3 may be connected thereto.

Each signal detection circuit 105 incorporates an amplification circuit for each signal line 3 (see FIG. 6), which amplifies the inputted electric signals. In the signal detection circuit 105, the electric signals inputted by the signal lines 3 are amplified by the amplification circuits and are converted to digital signals by an analog-to-digital converter (ADC).

A control section 106 is connected to the signal detection circuit 105 and the scan signal control circuit 104. The control section 106 applies predetermined process, such as noise reduction and the like, to the digital signals converted by the signal detection circuit 105. Further, the control section 106 outputs control signals representing signal detection timings to the signal detection circuit 105, and outputs control signals representing scan signal output timings to the scan signal control circuit 104.

The control section 106 of the present exemplary embodiment is configured by a microcomputer, and is provided with a central processing unit (CPU), a ROM, a RAM and a non-volatile memory section configured by flash memory or the like. The control section 106 executes a program stored in the ROM with the CPU, and thus performs control for imaging a radiographic image. The control section 106 applies process to interpolate image data for the radiation detection pixels 20B (interpolation processing) to the image data, to which the above-mentioned predetermined processing has been applied, and generates an image representing the irradiated radiation. Namely, the control section 106 generates the image representing the irradiated radiation by interpolating image data for the radiation detection pixels 20B on the basis of the image data to which the above-mentioned predetermined processing has been applied.

Figure 4:
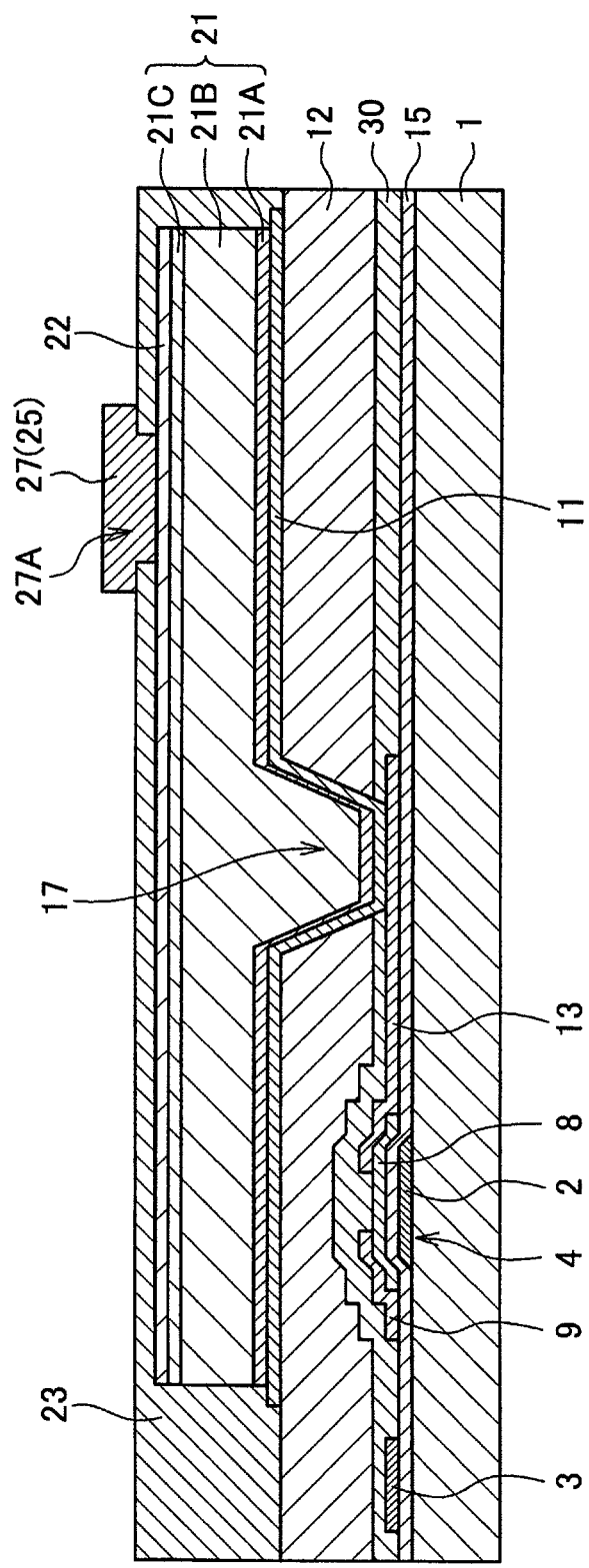
FIG. 4 is a sectional view of a radiation detector according to the present exemplary embodiment.
Figure 5:
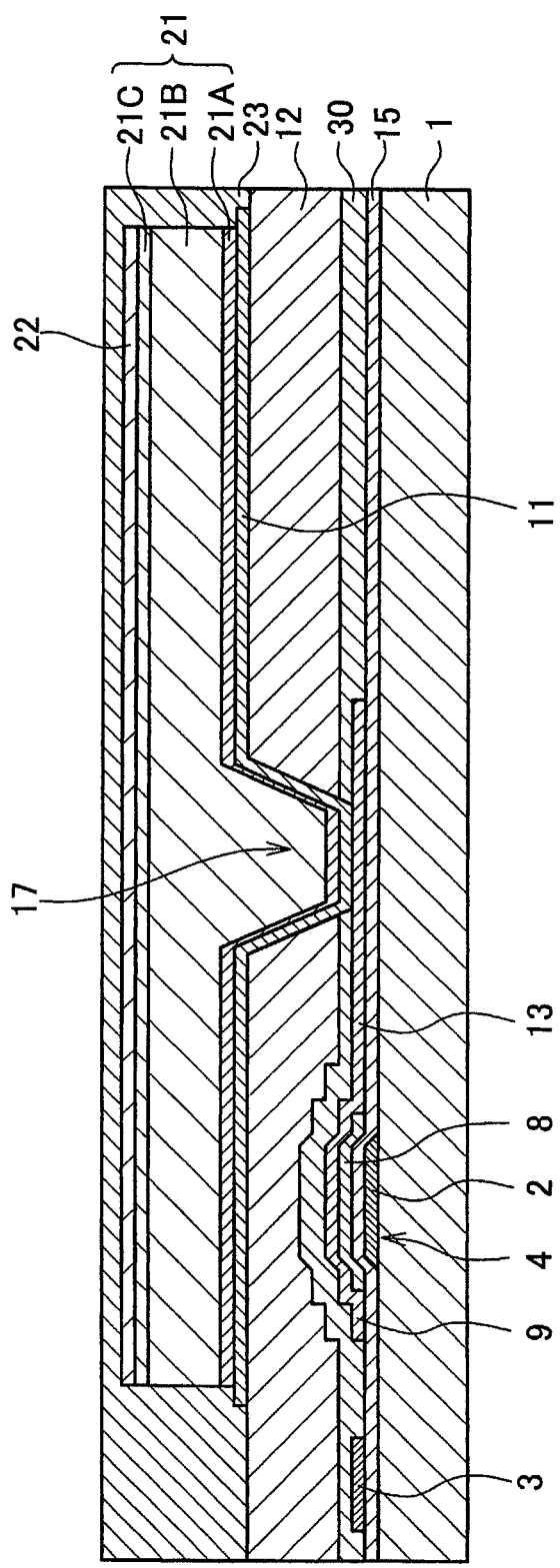
FIG. 5 is a sectional view of a radiation detector according to the present exemplary embodiment.

FIG. 3 shows a plan diagram illustrating configuration of the indirect-conversion-type radiation detector 10, in accordance with the present exemplary embodiment. FIG. 4 shows a sectional diagram of one of the radiographic imaging pixels 20A taken along line A-A in FIG. 3. FIG. 5 shows a sectional diagram of one of the radiation detection pixels 20B taken along line B-B in FIG. 3.

As illustrated in FIG. 4, at each pixel 20A of the radiation detector 10, the scan line 101 (see FIG. 3) and a gate electrode 2 are formed on the insulating substrate 1, formed of alkali-free glass or the like, and the scan line 101 is connected with the gate electrode 2 (see FIG. 3). A wiring layer in which the scan lines 101 and the gate electrodes 2 (hereinafter referred to as "the first wiring layer") is formed using Al or Cu or a layered film made mainly of Al or Cu. However, the material of the first wiring layer is not limited to these.

An insulating layer 15 is formed over the whole of the first signal layer. Portions of the insulating layer 15 that are disposed above the gate electrodes 2 operates as gate insulation films of the TFT switches 4. The insulating layer 15 is formed of, for example, SiNx or the like, and is formed by, for example, chemical vapor deposition (CVD) film formation.

Semiconductor active layers 8 are formed on the insulating layer 15 as islands over the gate electrodes 2. The semiconductor active layers 8 are channels portions of the TFT switches 4 and include amorphous silicon films, for example.

Source electrodes 9 and drain electrodes 13 are formed in a layer thereabove. The signal lines 3 are also formed in the wiring layer in which the source electrodes 9 and the drain electrodes 13 are formed. The source electrodes 9 are connected to the signal lines 3 (see FIG. 3). The wiring layer in which the source electrodes 9, drain electrodes 13 and signal lines 3 are formed (hereinafter referred to as "the second wiring layer") is formed using Al or Cu or a layered film made mainly of Al or Cu. However, the material of the second wiring layer is not limited to these. An impurity-doped semiconductor layer (not shown in the drawings), formed of impurity-doped amorphous silicon or the like, is formed between the source electrodes 9 and the semiconductor active layers 8 and between the drain electrodes 13 and the semiconductor active layers 8. According to the above, the TFT switches 4 for switching are configured. In the TFT switches 4, the source electrodes 9 and the drain electrodes 13 may be opposite due to the polarities of the charges that are collected and accumulated by lower electrodes 11.

A TFT protection film layer 30 is formed over substantially the whole area of a region in which the pixels 20 are provided on the substrate 1 (almost the whole region), covering the second wiring layer. The TFT protection film layer 30 is for protecting the TFT switches 4 and the signal lines 3. The TFT protection film layer 30 is formed of, for example, SiNx or the like, and is formed by, for example, CVD film formation.

A coated interlayer insulating film 12 is formed on the TFT protective film layer 30. The interlayer insulating film 12 is formed in a film thickness of 1 μm to 4 μm by a photosensitive organic material (e.g., a positive photosensitive acrylic resin: a material in which a naphthoquinone diazide positive photosensitizer is mixed together with a base polymer comprising a copolymer of methacrylic acid and glycidyl methacrylate) having a low permittivity (relative permittivity $\epsilon_r$=2 to 4).

In the radiation detector 10 according to the present exemplary embodiment, the capacitance between metals placed on top of and under the interlayer insulating film 12 is kept low by the interlayer insulating film 12. Further, usually this material also has a function as a planarizing film and also may planarize the steps formed below. In the radiation detector 10 according to the present exemplary embodiment, contact holes 17 are formed in positions in the interlayer insulating film 12 and the TFT protection film layer 30 opposing the drain electrodes 13.

Lower electrodes 11 of the sensor portions 103 are formed on the interlayer insulating film 12 in such a way as to cover the pixel regions while filling in the contact holes 17. The lower electrodes 11 are connected to the drain electrodes 13 of the TFT switches 4. The lower electrodes 11 have virtually no restrictions in their material as long as the material is conductive in a case where later-described semiconductor layers 21 are thick around 1 μm. For this reason, the lower electrodes 11 may be formed using a conductive metal such as an Al material or ITO.

On the other hand, in a case where the film thickness of the semiconductor layers 21 is thin (around 0.2 μm to 0.5 μm), light absorption may not be sufficient in the semiconductor layers 21. For this reason, in order to prevent an increase in leak current resulting from the application of the light to the TFT switches 4, it is preferable for the lower electrodes 11 to be formed using a layered film or an alloy made mainly of a light-blocking metal.

The semiconductor layers 21, which function as photodiodes, are formed on each lower electrodes 11. In the present exemplary embodiment, photodiodes with a PIN structure, in which an n$^+$layer, an i layer, and a p$^+$layer (n$^+$amorphous silicon, amorphous silicon, and p$^+$amorphous silicon) are layered, are employed as the semiconductor layers 21. The semiconductor layers 21 are formed by sequentially layering an n$^+$layer 21A, an i layer 21B, and a p$^+$layer 21C from the lower layer. The i layer 21B generates charges (a free electron and free hole pair) as a result of being light being applied to the i layer 21B. The n$^+$layer 21A and the p$^+$layer 21C function as contact layers, and electrically connect the i layer 21B to the lower electrode 11 and a later-described upper electrode 22.

Upper electrodes 22 are individually formed on each of the semiconductor layers 21. A material whose light transmittance is high, such as ITO or IZO (indium zinc oxide), for example, is used for the upper electrodes 22. In the radiation detector 10 according to the present exemplary embodiment, the sensor portions 103 are configured to include the upper electrodes 22, the semiconductor layers 21, and the lower electrodes 11.

A coated interlayer insulating film 23 is formed on the interlayer insulating film 12, the semiconductor layers 21, and the upper electrodes 22 in such a way as to have openings 27A in portions corresponding to the upper electrodes 22 and in such a way as to cover each of the semiconductor layers 21.

The common electrode lines 25 are formed on the interlayer insulating film 23 by Al or Cu or by an alloy or a layered film made mainly of Al or Cu. Contact pads 27 are formed in the neighborhoods of the openings 27A, and the common electrode lines 25 are electrically connected to the upper electrodes 22 via the openings 27A in the interlayer insulating film 23.

On the other hand, in each radiation detection pixel 20B of the radiation detector 10, as shown in FIG. 5, the TFT switch 4 is formed such that the source electrode 9 and the drain electrode 13 are in contact. Namely, in the pixel 20B, the source and drain of the TFT switch 4 are short-circuited. Accordingly, charges collected at the lower electrode 11 of the pixels 20B flow into the signal lines 3 regardless of the switching state of the TFT switches 4.

On the radiation detector 10 that has been formed as described above, a protective film is further formed, if necessary, by an insulating material whose light absorption is low, and a scintillator comprising GOS or the like is adhered on the surface of the protective film using an adhesive resin whose light absorption is low.

Figure 6:
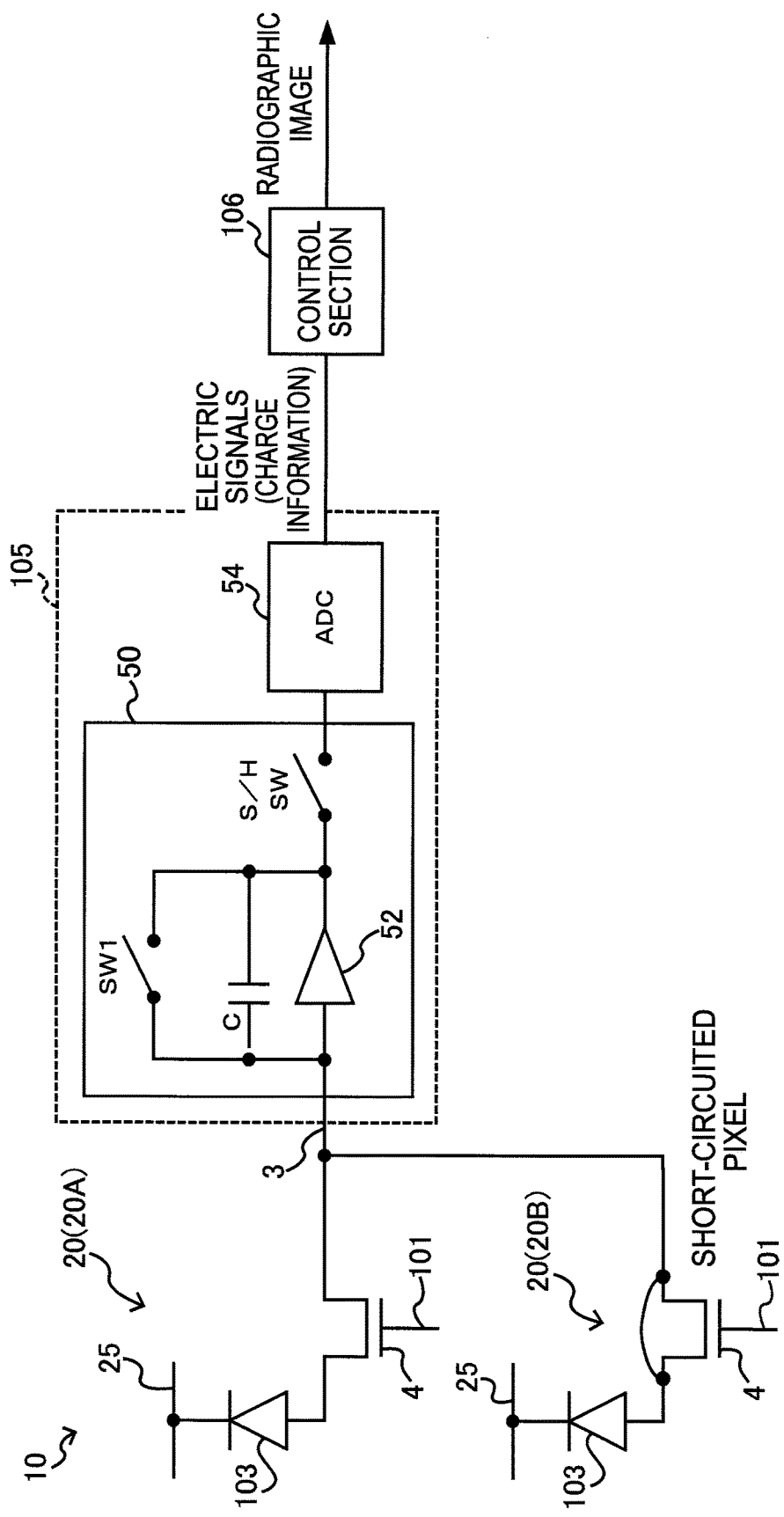
FIG. 6 is a schematic configurational diagram showing a signal detection circuit of the radiographic imaging device according to the present exemplary embodiment.

Next, configuration of the signal detection circuit 105 of the present exemplary embodiment is described. FIG. 6 is a schematic configurational diagram of an example of the signal detection circuit 105 of the present exemplary embodiment. The signal detection circuit 105 of the present exemplary embodiment is configured to include an amplification circuit 50 and an analog-to-digital converter (ADC) 54. Although not illustrated in FIG. 6, the amplification circuit 50 is provided for each signal line 3. Namely, the signal detection circuit 105 is configured to include the same number of plural amplifier circuits 50 as the number of signal lines 3 in the radiation detector 10.

The amplification circuit 50 is constituted by a charge amplification circuit. The amplification circuit 50 is provided with an amp 52 such as an operational amp or the like, a capacitor C connected in parallel with the amp 52, and a charge reset switch SW1 connected in parallel with the amp 52.

In the amplification circuit 50, when the charge reset switch SW1 is in the OFF state, charges (electric signals) are read out by the TFT switches 4 of the pixels 20. Then, the charges read out by the TFT switches 4 are accumulated at the capacitor C, and a voltage value outputted from the amp 52 in accordance with the accumulated charge amount is amplified.

The control section 106 applies a charge reset signal to the charge reset switch SW1 and performs control to switch the charge reset switch SW1 ON and OFF. Note that in a case in which the charge reset switch SW1 is switched ON, the input side and output side of the amp 52 are shorted together, and charges at the capacitor C are discharged.

The ADC 54 converts electric signals that are analog signals inputted from the amplification circuit 50 to digital signals, in a state in which a sample-hold (S/H) switch SW is switched ON. The ADC 54 serially outputs the electric signals converted to digital signals to the control section 106.

The electric signals outputted from all the amplification circuits 50 provided in the signal detection circuit 105 are inputted to the ADC 54 of the present exemplary embodiment. Namely, the signal detection circuit 105 of the present exemplary embodiment is provided with a single ADC 54 regardless of the number of amplification circuits 50 (and signal lines 3).

In the present exemplary embodiment, electric signals (charge information) from the signal lines 3 connected to the radiation detection pixels 20B (in FIG. 2, one or both of D2 and D3; for example, D2) are detected by the amplification circuits 50 of the signal detection circuit 105. The control section 106 compares the values of the digital signals converted by the signal detection circuit 105 with a pre-specified threshold value for radiation detection. Then, the control section 106 determines whether radiation has been irradiated in accordance with whether the values of the digital signals are above the threshold value or not. Therefore, in the present exemplary embodiment, a control signal from the control device 202 are not required for detection of the irradiation of the radiation, and therefore, is configured to be "synchrony-free". The determination by the control section 106 of whether or not radiation has been irradiated, is not limited to this comparison with a radiation detection threshold value. For example, the control section 106 may detect the irradiation of radiation on the basis of a pre-specified condition, such as a number of detections or the like.

Note that the meaning of the term "detection" of electric signals in the present exemplary embodiment is intended to include sampling of the electric signals.

Figure 7:
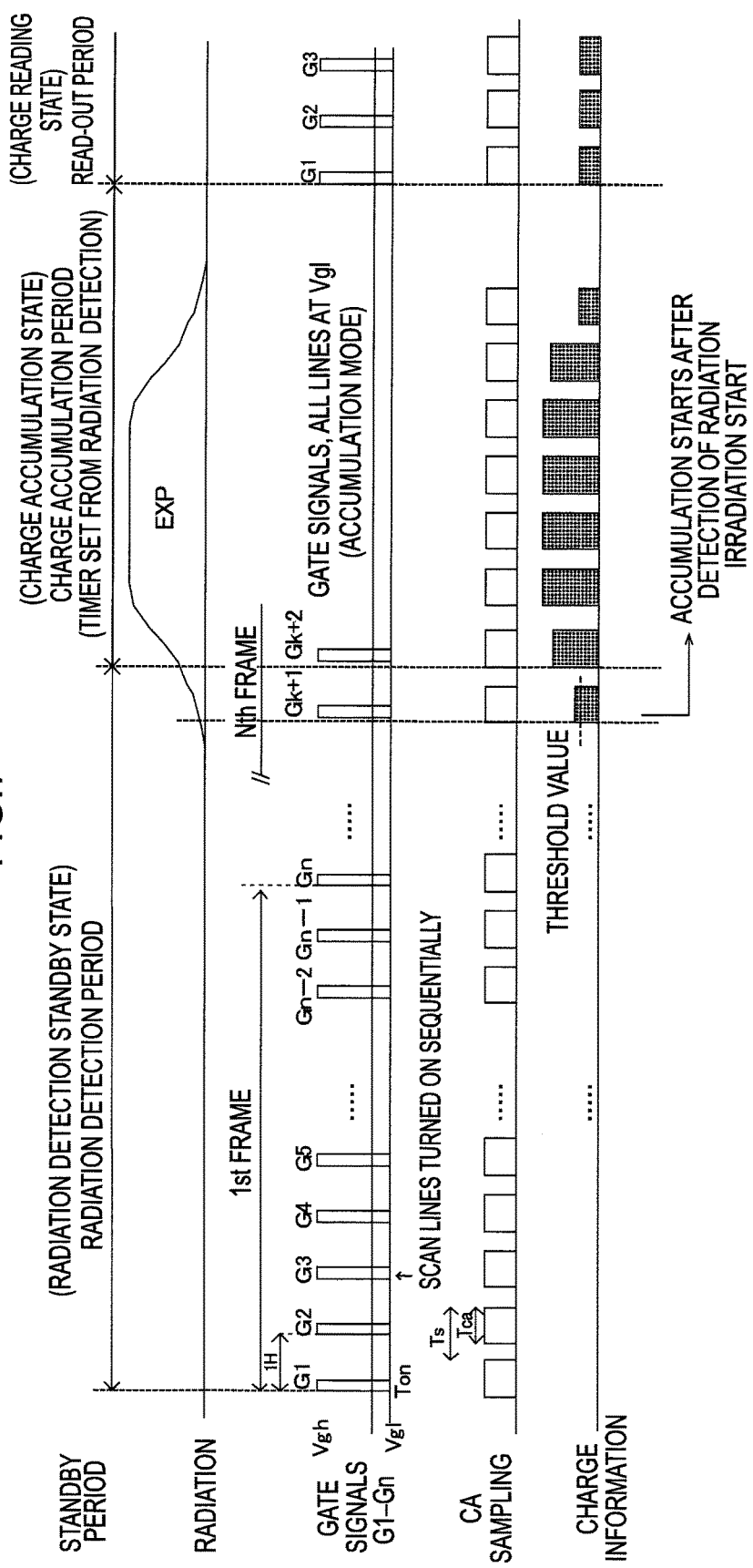
FIG. 7 is a timing chart showing a flow of operations when radiation is irradiated (for imaging a radiographic image) at the radiographic imaging device according to the present exemplary embodiment.
Figure 8:
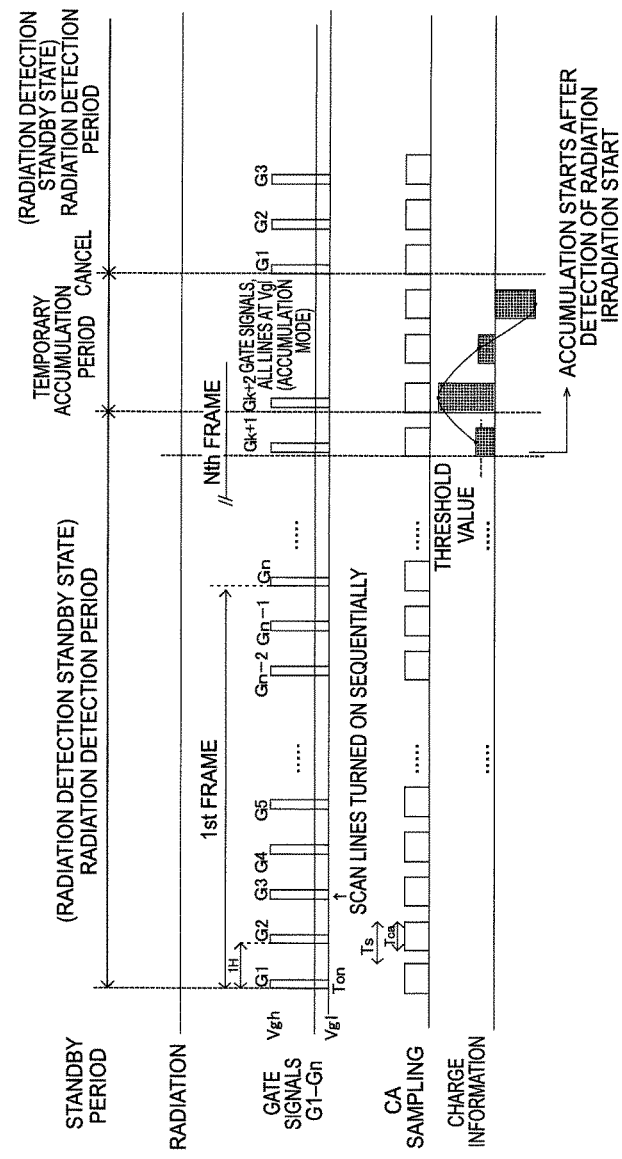
FIG. 8 is a timing chart showing a flow of operations when charges are generated by noise caused by interference at the radiographic imaging device according to the present exemplary embodiment.

Next, the flow of operations during imaging of a radiographic image by the radiographic imaging device 100 with the configuration described above, will be described with reference to FIG. 7 to FIG. 11, focusing on an operation for detecting the start of the irradiation of the radiation. FIG. 7 is a timing chart showing an example of a flow of operations when the radiation is irradiated (if a radiographic image is being imaged). FIG. 8 is a timing chart showing an example of a flow of operations when charges are generated by noises due to interference or the like. Further, FIG. 9 is a flow-chart showing a flow of operations when imaging a radiographic image.

The radiographic imaging device 100 detects the start of an irradiation of radiation, accumulates charges in the pixels 20 of the radiation detector 10, and outputs a radiation image based on image data according to the accumulated charges. Thus, the radiographic imaging device 100 images a radiographic image.

Figure 9:
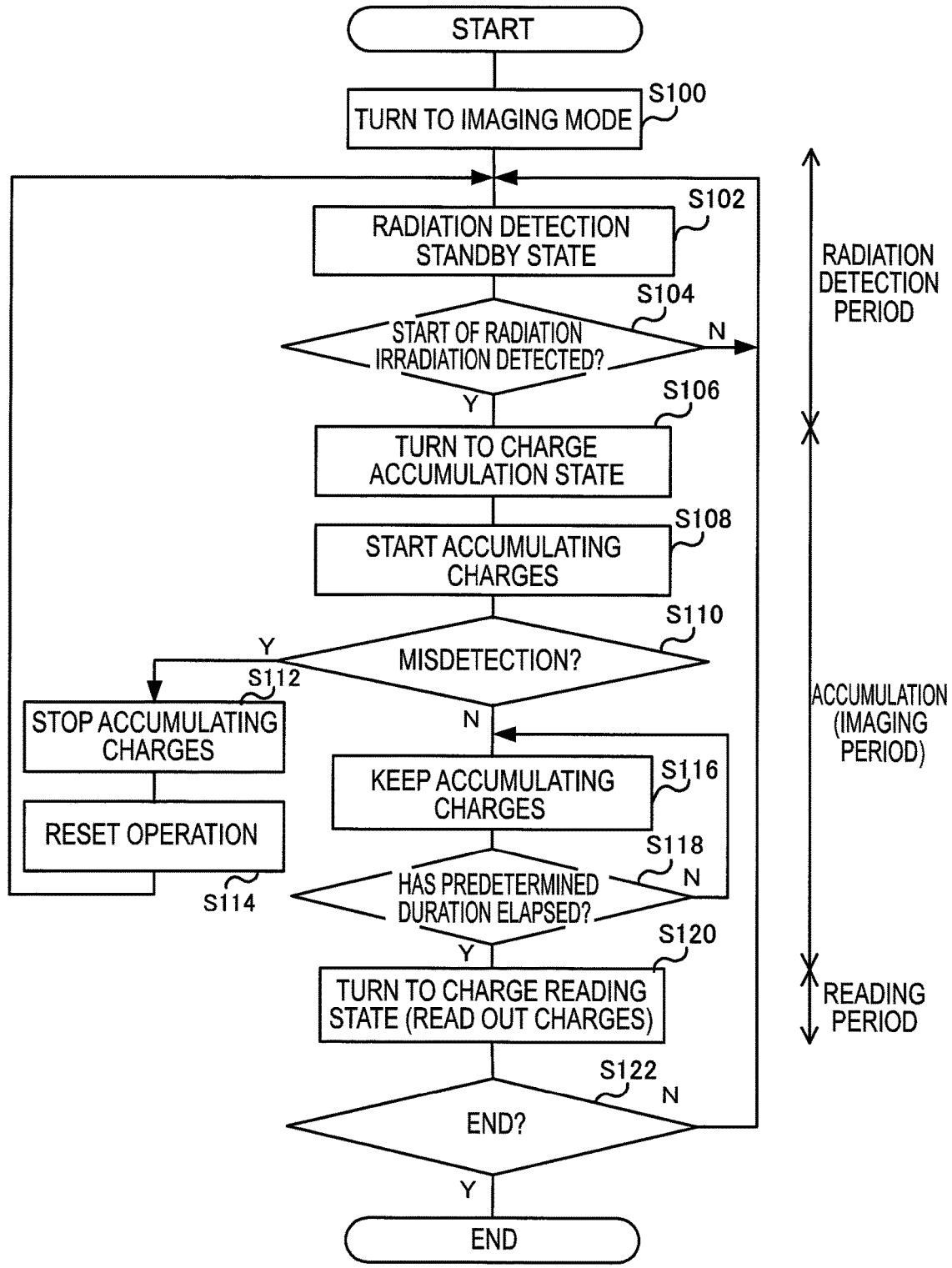
FIG. 9 is a flow-chart showing a flow of operations when imaging a radiographic image according to the present exemplary embodiment.

In the present exemplary embodiment, in a case in which a radiographic image is to be imaged, the radiographic imaging device 100 is turned to an imaging mode by the control device 202 (FIG. 9, step S100). When the radiographic imaging device 100 is turned to the imaging mode, the radiographic imaging device 100 turns to a radiation detection standby state for detecting the radiation (FIG. 9, step S102). Then, when the radiographic imaging device 100 detects irradiation of radiation (FIG. 9, Yin step S104), the radiographic imaging device 100 turns to a charge accumulation state for accumulating charges in the radiation detector 10 (FIG. 9, Yin step S106). Further, a predetermined duration after the detection of the radiation (FIG. 9, Yin step S118), the radiographic imaging device 100 turns to a charge reading state for reading out the accumulated charges (FIG. 9, step S120). When the reading of charges is completed, and if the radiation image is still to be imaged, the radiographic imaging device 100 turns to a standby state (FIG. 9, N in step S122). However, if not, the radiographic imaging device 100 ends the present process (FIG. 9, Yin step S122).

When radiation is irradiated from the radiation irradiation device 204, the irradiated radiation is absorbed by the scintillator and is converted to visible light. The radiation may be irradiated from a front side or rear side of the radiation detector 10. The light that has been converted to visible light by the scintillator is illuminated onto the sensor portions 103 of the pixels 20.

When light is illuminated, charges are generated inside the sensor portions 103. Then, the generated charges are collected by the lower electrodes 11.

In each radiographic imaging pixel 20A, the drain electrode 13 and the source electrode 9 are not shorted together. Therefore, the charges collected at the lower electrode 11 are accumulated in the radiographic imaging pixel 20A. In contrast, in each radiation detection pixel 20B, the drain electrode 13 and the source electrode 9 are shorted together. Therefore, the charges collected at the lower electrode 11 of the pixel 20B flow into the signal line 3.

In the radiographic imaging device 100 of the present exemplary embodiment, electric signals (charge information) outputted from the radiation detection pixels 20B are detected at the amplification circuits 50 of the signal detection circuit 105, as described above. Then, the control section 106 compares the detected electric signals (charge information) with the pre-specified threshold value for radiation detection, and determines whether an irradiation of radiation has started, based on whether or not the electric signals are above the threshold value (FIG. 9, step S104). As shown in FIG. 7, FIG. 8, and FIG. 9 in a case in which the start of an irradiation of radiation is detected (FIG. 9, Yin step S104), the radiographic imaging device 100 switches into an accumulation period for accumulating the charges generated by the sensor portions 103 (see Gk+2 in FIG. 7 and in FIG. 8, and S106 of FIG. 9). Note that, in the present exemplary embodiment, since the accumulation period is a period for accumulating charges for imaging, this period may also be referred to as "imaging period".

In the radiographic imaging device 100 of the present exemplary embodiment, leak currents may be generated in the sensor portions 103. Accordingly, as shown in FIG. 7 and FIG. 8, in the radiation detection period, ON signals are sequentially outputted to the scan lines 101 and are sequentially applied to the gate electrodes 2 of the TFT switches 4, and the charges are outputted from the sensor portions 103 with intervals of a constant period. Thus, the radiographic imaging device 100 performs a reset operation that resets the charges accumulated at the sensor portions 103.

In a case in which the start of an irradiation of radiation is detected, and the radiographic imaging device 100 is turned into the accumulation period, the control section 106 instructs the radiation detector 10 to accumulate the charges (FIG. 9, step S108). In the radiographic imaging pixels 20A of the radiation detector 10, since the TFT switches 4 are maintained in the OFF state, the radiographic imaging pixels 20A accumulates the charges. In contrast, since the TFT switches 4 of the radiation detection pixels 20B are short-circuited, the radiation detection pixels 20B output charges to the signal detection circuit 105 even in the charge accumulation period (in which the TFT switches 4 are OFF). A sample-hold switch SW5 is switched ON and OFF with a predetermined timing, regardless of whether the radiographic imaging device 100 is in the charge accumulation period or a reading period (see the sampling CA in FIG. 7 and FIG. 8). Accordingly, information of the charges outputted from the radiation detection pixels 20B is inputted to the control section 106 in the form of electric signals (charge information) via the amplification circuits 50 and ADC 54 of the signal detection circuit 105.

When the radiation is being irradiated (a radiographic image is imaged), the radiographic imaging device 100 of the present exemplary embodiment determines when the predetermined duration has passed from the start of the irradiation of radiation was detected, with a timer (not shown in the drawings) (FIG. 9, step S118). When the predetermined duration has not passed (FIG. 9, N in step S118), the radiographic imaging device 100 keeps accumulating the charges (FIG. 9, step S116). On the other hand, when the predetermined duration has passed (FIG. 9, Yin step S118), the radiographic imaging device 100 ends the accumulation period, and turns to the reading period for reading the accumulated charges from the pixels 20A (FIG. 9, step 120). Specifically, in the reading period, the radiographic imaging device 100 sequentially applies ON signals to the gate electrodes 2 of the TFT switches 4 via the scan lines 101. Accordingly, the TFT switches 4 of the pixels 20A sequentially are switch ON, and the radiographic imaging device 100 reads out the charges, by electric signals being outputted to the signal lines 3 in accordance with charge amounts accumulated in the pixels 20A.

On the other hand, a case in which the start of the irradiation of the radiation being misdetected due to noise will be described. Due to impact or interference of electromagnetic waves or the like, charges exceeding the threshold value may be generated by noises (charges) that are generated in the sensor portions 103 (see Gk+2 in FIG. 8). Electric signals (charge information) based on noises (charges) generated due to interference have different characteristics from electric signals (charge information) based on charges generated due to irradiation of radiation during usual imaging of a radiographic image. In particular, a time variation is different. For example, as can be seen by comparing FIG. 7 with FIG. 8, the polarity of electric signals may be opposite from the usual polarity, because of charges may flow in reverse if it is a noise. Further, if it is a noise, the amplitude of a waveform expressed by the time variation of the electric signals (charge information) oscillates, as shown in FIG. 8.

Figure 11:
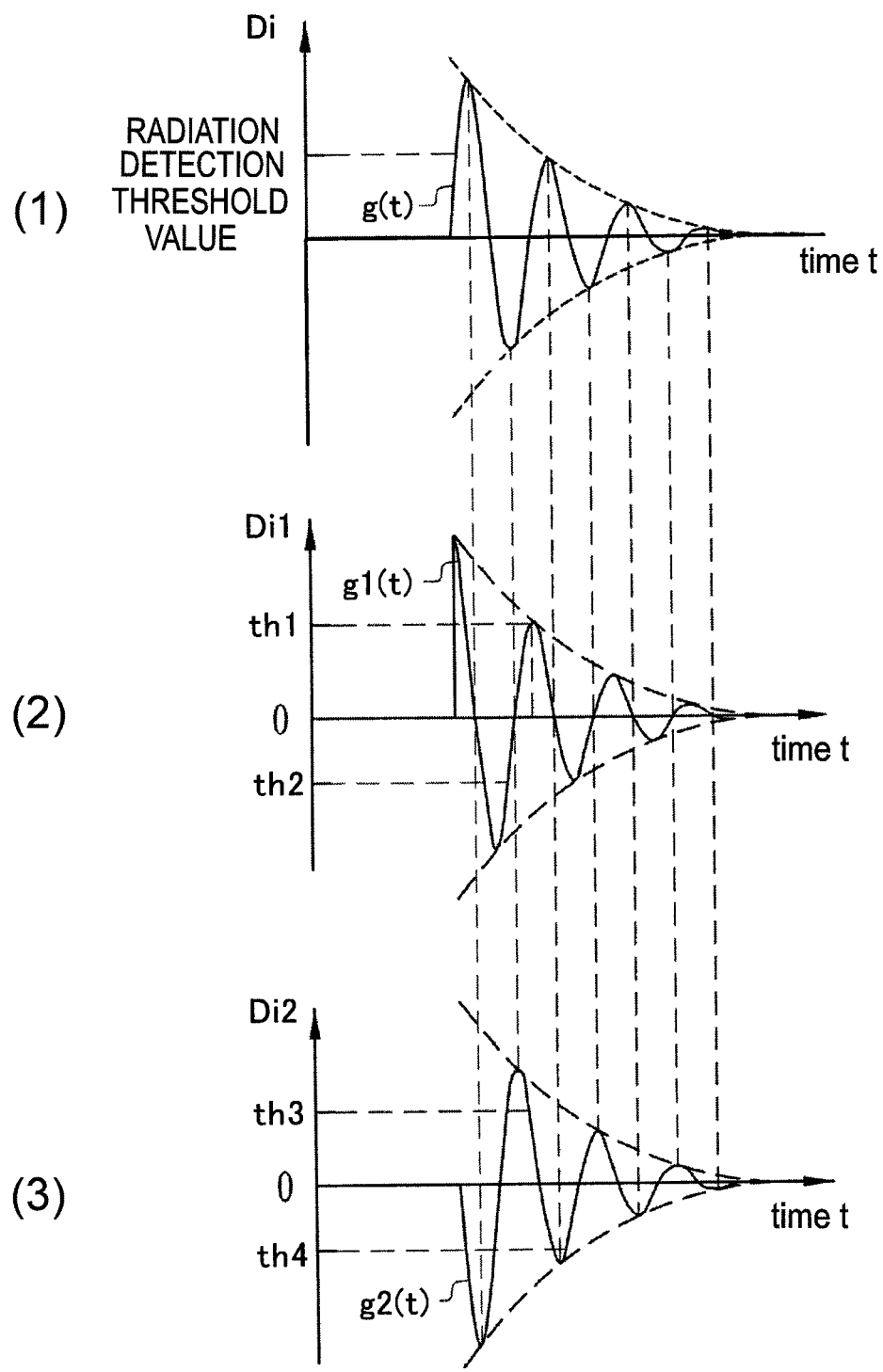
FIG. 11 is a graph showing time variations of the electric signals when noise is generated in the radiographic detector according to the present exemplary embodiment.

Hereinafter, the difference between the electric signals caused by irradiation of the radiation and the electric signals caused by noises, in the radiation detector 10 of the present exemplary embodiment, will be described. FIG. 10 is a graph showing time variations of the electric signals when radiation is irradiated to the radiographic detector 10 according to the present exemplary embodiment. Note that, (1), (2), and (3) of FIG. 10 shows the time variation of, electric signal Di, primary differentiation Di1 of electric signal Di, and secondary differentiation Di2 of electric signal Di, respectively. Further, FIG. 11 is a graph showing time variations of the electric signals when noise is generated in the radiographic detector 10 according to the present exemplary embodiment. Note that, (1), (2), and (3) of FIG. 11 shows the time variation of, electric signal Di, primary differentiation Di1 of electric signal Di, and secondary differentiation Di2 of electric signal Di, respectively.

As shown in (1) of FIG. 10, when radiation is irradiated, the electric signal Di may be expressed as function f(t) of time t, since the electric signal Di increases and varies together with the time. In the present exemplary embodiment, the start of irradiation of the radiation is detected based on whether the electric signal Di exceeds a threshold value for radiation detection. Further, as shown in (1) of FIG. 11, when noise is generated, the electric signal Di may be expressed as function g(t) of time t, since the electric signal Di varies together with the time, as the electric signal Di when radiation is irradiated. However, the electric signal Di cased by noise has a damped oscillatory waveform, which is a sing wave with a constant frequency and a decaying amplitude. When this the electric signal Di cased by noise is primary differentiated, waveform g1(t) is obtained that has a phase difference of 90 degree from the electric signal Di, as shown in (2) of FIG. 11.

As shown in (2) of FIG. 10, when radiation is irradiated, f1(t) which is a primary differentiation of function f(t) rises rapidly after that start of irradiation of the radiation and soon becomes constant. On the other hand, as shown in (2) of FIG. 11, when noise is generated, g1(t) which is a primary differentiation of function g(t) also has damped oscillatory waveform with a phase difference of 90 degree. Further, when radiation is irradiated, primary differentiation f1(t) always has a positive polarity. On the other hand, when noise is generated, the primary differentiation g1(t) has an amplitude that traverses between positive and negative polarity back and forth.

Further, as shown in (3) of FIG. 10, when radiation is irradiated, f2(t) which is a secondary differentiation of function f(t) has a characteristic like a Gaussian function. On the other hand, as shown in (3) of FIG. 11, when noise is generated, g2(t) which is a secondary differentiation of function g(t) also has damped oscillatory waveform with phase difference like the primary differentiation g1(t). Accordingly, as in the primary differentiation, when radiation is irradiated, the secondary differentiation f2(t) always has the positive polarity. On the other hand, when noise is generated, the secondary differentiation g2(t) once has a negative polarity, then has an amplitude that traverses between positive and negative polarity back and forth.

Note that, as can be understood when FIGS. 10 and 11 are compared, the amplitude of the primary differentiation f1(t) (when radiation is irradiated) is smaller than the amplitude of the primary differentiation g1(t) (when noise is generated). Similarly, the amplitude of the secondary differentiation f2(t) (when radiation is irradiated) is smaller than the amplitude of the secondary differentiation g2(t) (when noise is generated). Accordingly, the determination of misdetection (noise) may be made by previously setting threshold values for misdetection determination (th1, and th2) for distinguishing the primary differentiation f1(t) and the primary differentiation g1(t), and by determining as a misdetection if the time variation of the electric signals exceeds the threshold values for misdetection determination. Similarly, the determination of misdetection (noise) may be made by previously setting threshold values for misdetection determination (th3, and th4) for distinguishing the secondary differentiation f2(t) and the secondary differentiation g2(t), and by determining as a misdetection if the time variation of the electric signals exceeds the threshold values for misdetection determination.

In the present exemplary embodiment, the detection of the electric signals (charge information) outputted from the radiation detection pixels 20B continues after turning to the accumulation period. Accordingly, in the present exemplary embodiment, the control section 106 determines whether the start of the irradiation of the radiation has been misdetected or not, based on whether the time variation of the electric signals (charge information) for a predetermined detection period has a feature characteristics of noise, as described above (FIG. 9, step S110). Specifically, as mentioned above, the determination of misdetection may be performed by determining whether or not the polarity of the electric signals is opposite to the usual polarity in the detection period. Further, the determination of misdetection may be performed by differentiating (for example, primary differentiation or secondary differentiation) the amplitudes of the electric signals (charge information) outputted in the detection period and, if the gradient is substantially constant or progressively increasing, determining that the start of an irradiation of radiation has been properly detected, and if the gradient is decreasing, determining that the start of an irradiation of radiation has been misdetected. Furthermore, the determination of misdetection may be performed by using a threshold value for determination of misdetection. Note that, in order to further raise the detection accuracy, plural kinds of detection may be combined.

The predetermined detection period (imaging period) for detecting the electric signals differs depending on imaging conditions and on the radiographic imaging device 100 and the like. Accordingly, for example, a percentage of imaging periods or the like may be determined by prior testing or the like.

Further, in a case in which a strong impact is experienced as interference, charges appear in particular signal lines 3, and the noise that is produced differs between the signal lines 3. In such case, noises that are generated in the signal lines 3 may be previously obtained by testing and the like, and determination criteria may be set differently between the signal lines 3. For example, the above mentioned threshold values for determination of misdetection (th 1 to th 4) may be predetermined for each of the signal lines 3. In such case, for example, based on the position of the signal lines, the plural signal lines 3 may be divided into plural regions, such as, for example, end portion region of the end portion of the radiation detector 10, and central region of the center of the radiation detector 10. In this case, each region may have different threshold value for determination of misdetection. In the case in which the threshold values for determination of misdetection differ for each signal line 3 or for each region, the determination of misdetection is executed for each signal line 3 or for each region. In such case, the accumulation period may be cancelled when the determination of misdetection is made for once or for a predetermined times.

In the radiographic imaging device 100 of the present exemplary embodiment, in a case in which it is determined that there has been a misdetection (FIG. 9, Yin step S110), the accumulation period is cancelled, the accumulation of charge information stops (FIG. 9, step S112), and the radiographic imaging device 100 turns to the radiation detection period, as shown in FIG. 8.

In the case shown in FIG. 8, the radiographic imaging device 100 ends the accumulation period and immediately turns to the radiation detection period. However, in order to prevent an error in the determination of the start of the irradiation of the radiation due to charges accumulated in this accumulation period, the above-mentioned reset operation may be carried out before the turning to the radiation detection period, and electric signals (charge information) may be read out and discarded (FIG. 9, step S114). In this case, the period of the reset operation becomes a period in which the radiation is not detected (a non-detection period). Therefore, in order to shorten the non-detection period, the reset operation may be carried out simultaneously for plural scan lines 101.

The control device 202 may perform control so as to prohibit the irradiation of radiation from the radiation irradiation device 204 during the reset operation.

As described above, in the radiographic imaging device 100 of the present exemplary embodiment, when radiation is irradiated, electric signals (charge information) outputted from the radiation detection pixels 20B in the charge accumulation period, from charges generated in accordance with the irradiation, are detected by the signal detection circuit 105 during a predetermined detection period. The control section 106 determines whether or not time variation of the electric signals (charge information) has a pre-specified characteristic of noises. If the control section 106 determines that the electric signals do not have the pre-specified characteristic, it is determined that the start of the irradiation of radiation has been properly detected. Accordingly, the charge accumulation period continues and a radiographic image is imaged. On the other hand, if the control section 106 determines that the electric signals have the pre-specified characteristic, and thus are noises, the control section 106 determines that the start of the irradiation of the radiation has been misdetected, stops (cancels) the charge accumulation period, and turns to the radiation detection period.

Accordingly, in the present exemplary embodiment, it may be determined whether a detection of the start of an irradiation of radiation is a misdetection caused by noise due to interference or the like, on the basis of the electric signals (charge information) outputted from the radiation detection pixels 20B during the charge accumulation period. Therefore, the present exemplary embodiment may accurately detect the start of the irradiation of the radiation, even in a case in which noises due to interference or the like occurs.

In the present exemplary embodiment, if a misdetection is determined, the charge accumulation period is stopped (cancelled) and the radiographic imaging device 100 turns to the radiation detection period. Therefore, the present exemplary embodiment may shorten the time until determination of a misdetection. If time is required until determination of misdetection, the radiation may be irradiated before the determination of misdetection. Consequently, when the radiographic image is imaged, the radiation may not be properly detected and proper radiographic image may not be obtained. In such a case, there is a risk of subjecting the imaging subject 206 to unnecessary exposure. However, the present exemplary embodiment may prevent the above risks.

Further, a case in which, starting the accumulation period after determining whether the detection was a misdetection when the irradiation of radiation has started, can be considered. However, in such case, the exposure the imaging subject 206 has received after the start of the irradiation of the radiation until the determination that the detection was not a misdetection is made, becomes an unnecessary exposure that does not contribute the radiographic image. On the other hand, as mentioned above, after the detection of the start of irradiation of the radiation, the present exemplary embodiment determines whether the detection was a misdetection or not, after turning into the accumulation period. Further, if it is determined that the detection was a misdetection, the present exemplary embodiment immediately stops the accumulation period, and returns to the radiation detection period. Accordingly, the present exemplary embodiment may accurately detect the start of irradiation of the radiation and may reduce unnecessary exposure due to real-time detection, when compared to a case in which the radiation detector 10 is tuned into accumulation period after determining whether the detection was a misdetection or not.

Moreover, if images based on noise are outputted as radiographic images, there may be risks of misdiagnoses, increase of service calls, and the like. However, with the present exemplary embodiment, images based on noise are not outputted. Therefore, the present exemplary embodiment may prevent these risks.

Figure 12:
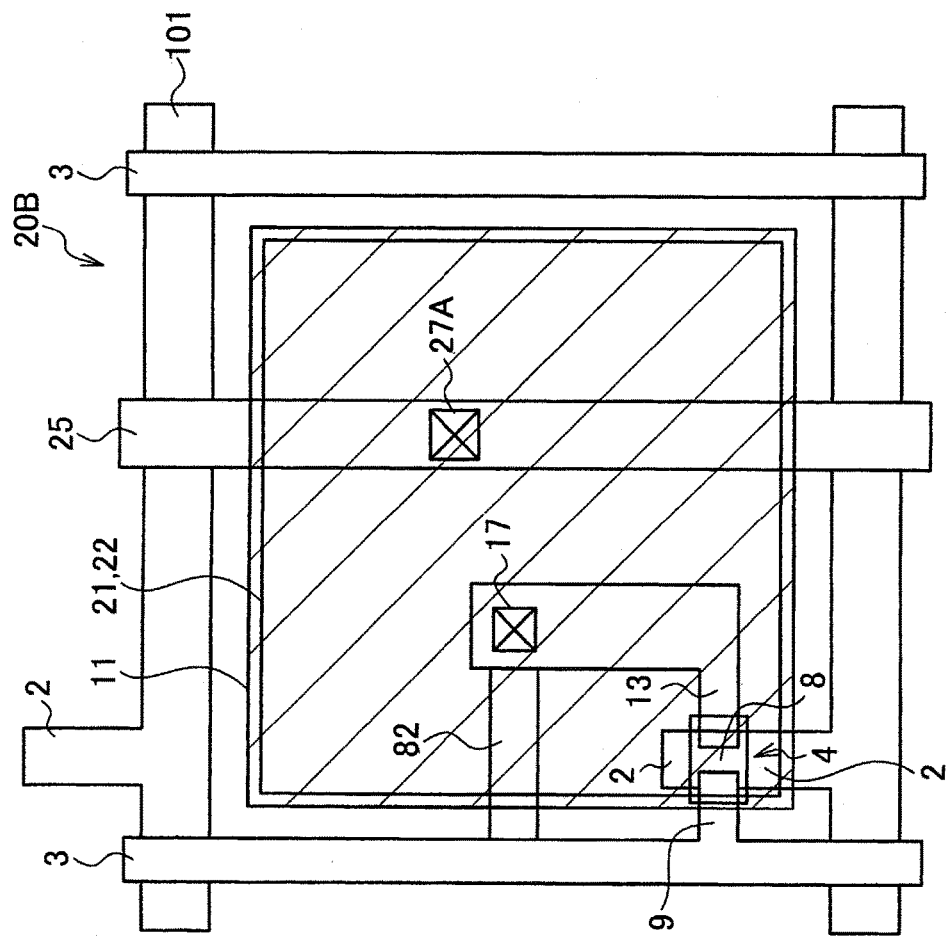
FIG. 12 is a plan view illustrating configuration of a radiation detector according to an alternative exemplary embodiment.
Figure 13:
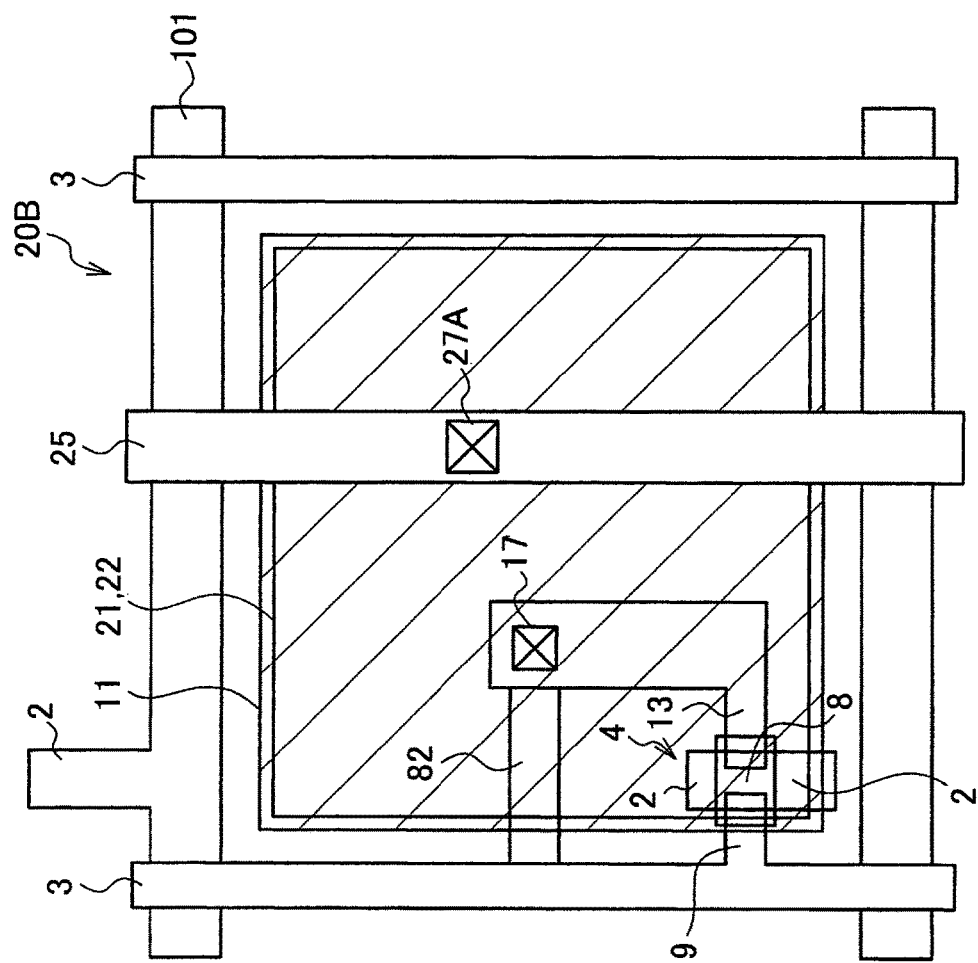
FIG. 13 is a plan view illustrating configuration of a radiation detector according to an alternative exemplary embodiment.

In the above exemplary embodiments, a case in which the radiation detection pixels 20B each including the TFT switch 4 having the source and drain shorted, is used for pixels 20 for the control section 106 to acquire electric signals during the charge accumulation period, has been described. However, the pixels 20 for acquiring electric signals during the charge accumulation period are not limited thereto. For example, as illustrated in FIG. 12, connection line 82 may be formed from partway along the drain electrode 13 and may be connected with the signal line 3. In this case, the source and drain of the TFT switch 4 are effectively short-circuited. When the source and drain of the TFT switch 4 are shorted together as described above and in FIG. 12, the gate electrode 2 may be formed to be separated from the scan line 101 as shown in FIG. 13.

Figure 14:
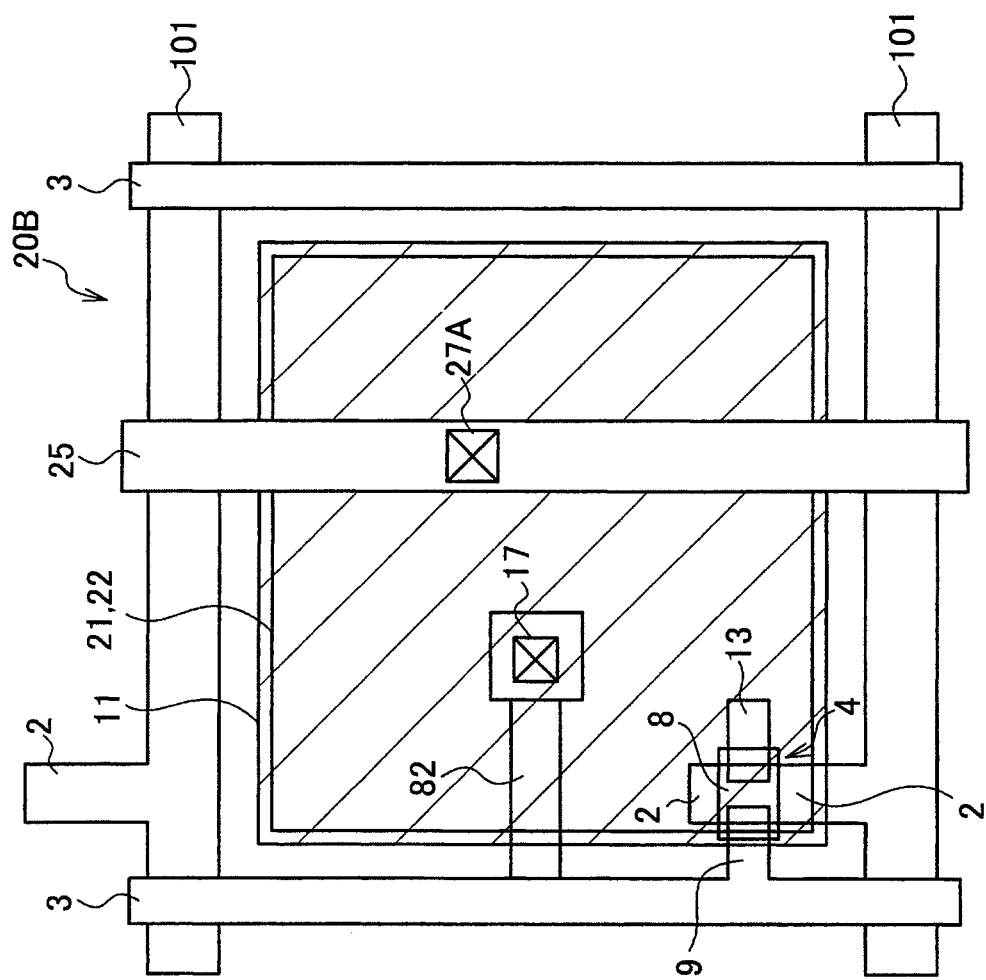
FIG. 14 is a plan view illustrating configuration of a radiation detector according to an alternative exemplary embodiment.

As an example, as shown in FIG. 14, in each radiation detection pixel 20B, the connection line 82 may be formed and the sensor portion 103 and signal line 3 may be connected via the connection line 82 and the contact hole 17, and the drain electrode 13 and contact hole 17 may be electrically disconnected.

In the above exemplary embodiments described, a case in which pixels having the TFT switches 4 short-circuited are employed as the radiation detection pixels 20B, has been described. However, pixels having the TFT switches 4 not short-circuited may be employed as the radiation detection pixels 20B. In this case, control of the TFT switches 4 of the pixels 20B may be performed separately from control of the TFT switches 4 of the pixels 20A. Furthermore, in this case, predetermined pixels 20 of the radiation detector 10 may be employed as the pixels 20B, or pixels other than the pixels 20 in the radiation detector 10 may be provided.

In the radiation detector 10 of the radiographic imaging device 100 of the present exemplary embodiment (see FIG. 2), the radiation detection pixels 20B are connected to some of the signal lines 3. However, the present invention is not limited thereto. The radiation detection pixels 20B may be provided at positions in which all of the signal lines 3 can be connected. Positions of the radiation detection pixels 20B are not limited by the above exemplary embodiment.

Further, in the above exemplary embodiment, a case in which an indirect-conversion-type radiation detector 10, that generate charges due to converted light, is applied as the present invention, has been described. However, the present invention is not limited thereto. For example, a direct-conversion type radiation detector 10 that uses materials, such as an amorphous selenium (a-Se) or the like, that directly coverts radiation to charges, as photo-electric conversion layer, that absorbs radiation and coverts to charge, may be applied to the present invention.

The configurations, operations, etc. of the radiographic imaging device 100 and the radiation detector 10 described in the above exemplary embodiments are examples, and may be suitably modified within a scope not departing from the spirit of the present invention.

The "radiation" of the present invention is not particularly limited by the present exemplary embodiments; X-rays, gamma rays and the like, may be employed.

What is claimed is:

1. A radiographic imaging device, comprising:
    a plurality of pixels, each pixel including:
        a sensor portion that generates charges in accordance with irradiated radiation, and
        a switching element that, in accordance with control signals, reads out the charges from the sensor portion and outputs the charges to a signal line;
    a radiation detection section that outputs electric signals in accordance with the irradiated radiation;
    a start detection section that detects a start of an irradiation of the radiation based on the electric signals output from the radiation detection section during a detection period;
    a determination section that, during a radiographic imaging period after the start detection section has detected the start of the irradiation of the radiation, determines whether or not the start detection section has misdetected the start of the irradiation of radiation, based on the electric signals output from the radiation detection section; and
    a switching section that immediately switches from the imaging period to the detection period in a case in which the determination section determines that the detection is a misdetection; wherein
    the determination section determines whether or not the detection is a misdetection based on a time variation of at least one of:
    a polarity of charges corresponding to the detected electric signals, or
    an amplitude of a waveform that expresses a time variation in a charge amount.

2. The radiographic imaging device according to claim 1, wherein the switching section ends the imaging period in a case in which the determination section determines that the detection is a misdetection.

3. The radiographic imaging device according to claim 1, wherein:
    the radiation detection section comprises some or all of the plurality of pixels;
    the start detection section detects the start of the irradiation of the radiation based on the electric signals corresponding to the charges output from the pixels; and
    the determination section determines whether or not that the detection is a misdetection based on a criterion predetermined for each specific signal line.

4. The radiographic imaging device according to claim 1, further comprising an output section that outputs the electric signals corresponding to the charges read out from the plurality of pixels during the imaging period, and in a case in which the determination section determines that the detection is a misdetection, discards the electric signals without outputting the electric signals.

5. A radiographic imaging system, comprising:
    an irradiation device that irradiates radiation; and
    a radiographic imaging device according to claim 1 that images a radiographic image in accordance with the irradiated radiation.

6. A non-transitory computer readable medium storing a program causing a computer to execute a process for controlling a radiographic imaging device including:
    a plurality of pixels, each pixel including a sensor portion that generates charges in accordance with irradiated radiation, and a switching element that, in accordance with control signals, reads out the charges from the sensor portion and outputs the charges to a signal line; and
    a radiation detection section that outputs electric signals in accordance with the irradiated radiation,
    the process comprising:
    detecting the start of an irradiation of the radiation based on the electric signals output from the radiation detection section during a detection period;
    determining, during a radiographic imaging period after the start detection section has detected the start of the irradiation of the radiation, whether or not the start of the irradiation of radiation has been misdetected, based on the electric signals output from the radiation detection section;
    determining whether or not the detection is a misdetection based on a time variation of at least one of:
    a polarity of charges corresponding to the detected electric signals, or
    an amplitude of a waveform that expresses a time variation in a charge amount; and
    switching from the imaging period to the detection period immediately in a case in which a determination is made that the detection was a misdetection.

7. A method for controlling a radiographic imaging device including:
    a plurality of pixels, each pixel including a sensor portion that generates charges in accordance with irradiated radiation, and a switching element that, in accordance with control signals, reads out the charges from the sensor portion and outputs the charges to a signal line; and
    a radiation detection section that outputs electric signals in accordance with the irradiated radiation, the method comprising:

detecting the start of an irradiation of the radiation based on the electric signals output from the radiation detection section during a detection period;

determining, during a radiographic imaging period after the start detection section has detected the start of the irradiation of the radiation, whether or not the start of the irradiation of radiation has been misdetected, based on the electric signals output from the radiation detection section;

determining whether or not the detection is a misdetection based on a time variation of at least one of:

a polarity of charges corresponding to the detected electric signals, or an amplitude of a waveform that expresses a time variation in a charge amount; and switching from the imaging period to the detection period immediately in a case in which a determination is made that the detection was a misdetection.

* * * * *